United States Patent
Kim et al.

[11] Patent Number: 5,849,915
[45] Date of Patent: Dec. 15, 1998

[54] BUPRENORPHINE ANALGESIC ANALOGUES

[75] Inventors: Yong Hae Kim; Jin Kyu Park, both of Seoul; Kwon Kim, Kyunggi-Do; Hee Sock Park, Taejeon, all of Rep. of Korea

[73] Assignee: Dong Kook Pharmaceutical Company, Ltd., Seoul, Rep. of Korea

[21] Appl. No.: 861,050

[22] Filed: May 21, 1997

[30] Foreign Application Priority Data

May 28, 1996 [KR]   Rep. of Korea ...................... 96-18134

[51] Int. Cl.⁶ ................................................ C07D 489/12
[52] U.S. Cl. .................................................................. 546/39
[58] Field of Search ................................................. 546/39

[56]  References Cited

U.S. PATENT DOCUMENTS

| | | | |
|---|---|---|---|
| 3,329,682 | 7/1967 | Bentley et al. | 546/39 |
| 3,433,791 | 3/1969 | Bentley et al. | 546/39 |
| 3,442,900 | 5/1969 | Bentley et al. | 546/39 |
| 5,552,406 | 9/1996 | Mendelson | 546/39 |

OTHER PUBLICATIONS

J.H. van den Hende et al., *J. Amer. Chem. Soc.*, 89:12, pp. 2901–2905, Jun. 7, 1967.
W. Fulmor et al., *J. Amer. Chem. Soc.*, 89:13, pp. 3322–3330, Jun. 21, 1967.
A. Cowan, et al., *Br. J. Pharmac.*, vol. 60, pp. 537–545, 1977.
A. Cowan, et al., *Br. J. Pharmac.*, vol. 60, pp. 547–554, 1977.
R.W. Houde, *Br. J. Clin. Pharmac.*, vol. 7, pp. 297s–308s, 1979.
C.W. Hutchins, et al., *J. Med. Chem.*, 24:7, pp. 773–777, Jul. 1981.
C.W. Hutchins, et al., *J. Med. Chem.*, 27:4, pp. 521–527, 1984.
E.J. Cone, et al., *J. Phar. Sci.*, 73:2, pp. 243–246, Feb. 1984.
K.W. Bentley, et al., *J. Amer. Chem. Soc.*, 89:13, pp. 3273–3280, Jun. 21, 1967.

*Primary Examiner*—Donald G. Daus
*Attorney, Agent, or Firm*—Kenyon & Kenyon

[57] ABSTRACT

The object of this invention is to provide novel buprenorphine analgesic analogues represented by following formula (I) and their non-toxic pharmaceutically acceptable salts.

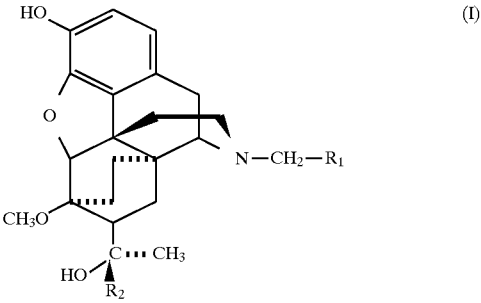

wherein $R_1$ is hydrogen atom, methyl, ethyl, cyclopropyl or cyclobutyl; and $R_2$ is cyclopropyl or cyclobutyl.

3 Claims, 3 Drawing Sheets

BUPRENORPHINE ANALGESIC ANALOGUES

(BACKGROUND OF THE INVENTION)

1. Field of the Invention

The present invention relates to novel buprenorphine analogues having better analgesia and less dependence, and their preparation methods which comprises reaction steps synthesized from thebaine as starting material.

2. Description of Prior Art

Buprenorphine having following structural formula(A), which was first synthesized in 1966 and has been marketed since 1978, has been regarded as an excellent anlagesic agent having improved analgesic efficacy compared to morphine with antagonistic property of morphine dependence.

(A)

Not a few researches have been performed regarding the analogues of buprenorphine to improve analgesic efficacy.

(SUMMARY OF THE INVENTION)

The object of this invention is to provide novel buprenorphine analgesic analogues represented by following formula (I) and their non-toxic pharmaceutically acceptable salts.

(I)

wherein $R_1$ is hydrogen atom, methyl, ethyl, cyclopropyl or cyclobutyl; and $R_2$ is cyclopropyl or cyclobutyl.

Among the analogues represented by formula(I), the desirable compounds are represented by following formulas (I)a, (I)b and (I)c.

(I)a (I)b (I)c

Each melting points of desirable compounds is compound (I)a: 262~265 °C., compound(I)b : 238~239, °C., and compound (I)c : 253~255°C.

(DETAILED DESCRIPTION OF THE INVENTION)

The novel buprenorphine analogues of the present invention can be prepared by following preparation method.

In case of $R_1$=hydrogen atom, the preparation method for compound of formula (I)'can be explained by following reaction scheme and process.

As shown in above rection scheme, thebaine of formula (II) is used as starting material. The compound of formula (III) is prepared according to Diels-Alder reaction using tebaine (II) and methyl vinyl ketone at 90~95% yield. Then, the compound of formula (IV) is prepared by hydrogenation reaction under palladium catalyst at 82~88% yield. By reacting Grignard reagent ($R_2MgX$) to the compound of formula (IV), the compound of formula (V) is obtained at 60~65% yield. Finally, the compound of formula (I)' can be obtained either heating compound of formula (V) at 220°~240° C. under diethylene glycol solvent and KOH base, or refluxing compound of formula (V) under DMF (dimethyl formamide) solvent and one of sodium n-butylmercaptide, sodium iso-propylmercaptide and sodium hydrosulfide base.

In case that $R_1$ is other than hydrogen atom, the preparation method requires a few more steps of reactions from compound of formula (V) as shown in following reaction scheme.

The compound of formula (VI) is prepared after replacing methyl radical in N position of compound of formula (V) with cyano radical.

The urea type compound of formula (VII) is prepared after reacting compound of formula (VI) with 28~32% of hydrogen peroxide in the presence of sodium hydroxide. Then, the compound of formula (VIII) is prepared by heating compound of formula (VII) at 165°~175° C. under diethylene glycol solvent and KOH base. The compound of formula (IX) is obtained by alkylation reaction of formula (VIII) with $R_1CH_2X$.

Finally, the compound of formula (I) can be obtained either heating compound of formula (IX) at 220°~240° C. under diethylene glycol solvent and KOH base, or refluxing compound of formula (IX) under DMF solvent and one of sodium n-butyl mercaptide, sodium iso-propylmercaptide and sodium hydrosulfide base.

To measure the analgesic efficacy of compound of formula (I), the compound of formula (I)a and the compound of formula (I)b were selected as testing materials. The methods and results of tests can be described as follows.

1. Hot plate Test for measuring analgesia (1) Method

Female mice weighing 18~22g were employed. The reaction time was measured from the mouse placing on the plate(55°±0.5°C.) until the appearance of behavioral response to the thermal nociceptive stimulus(licking hindpaws, jumping, flicking of paws). If no response was obtained in 30 sec, the mouse was discarded. The cut off time was 60 sec. Mice were tested prior to and 30 minutes after subcutaneous injection of compounds. $ED_{50}$ value was calculated using quantal criteria of analgesia.

(2) Result

Figure 1:
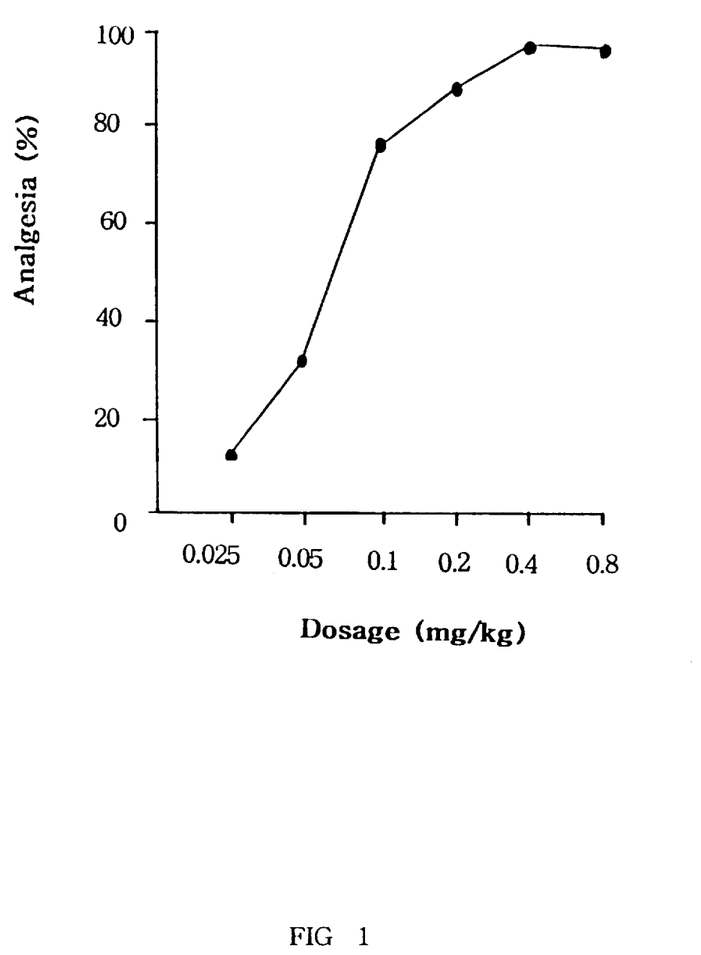
FIG. 1 shows the analgesic effect of compound of formula (I)a in the hot plate test in mice.

In the hot plate test, we found that the compound of formula (I)a produced a dose-dependent analgesic action. When the analgesic effect reached 100%, there was no reduction in effect with increasing of dosage. This property conformed to an agonist (FIG. 1). As shown in Table 1, the $ED_{50}$ value of compound of formula (I)a was about 1/100 of Morphine.

TABLE 1

| $ED_{50}$ value of compound of formula (I)a in the hot plate | |
| --- | --- |
| Compounds | $ED_{50}$ (95% confidence limits) |
| Compound of formula (I)a | 57.75 µg/kg (33.12~100.71) |
| Morphine | 5.81 mg/kg (3.43~9.86) |

2. Acetic Acid Writhing Test for measuring analgesia (1) Method

Male mice weighing 18~22g were employed in this test. Acetic acid in the concentration of 0.6% was injected by intra peritoneal (10 /kg). 5 minutes later, the frequeny of writhing during the following 10 minutes was recorded. Compounds studied were given by subcutaneous injection and served as control. Analgesia was expressed in terms of percentage of writhing frequency reduction.

(2) Result

Figure 2:
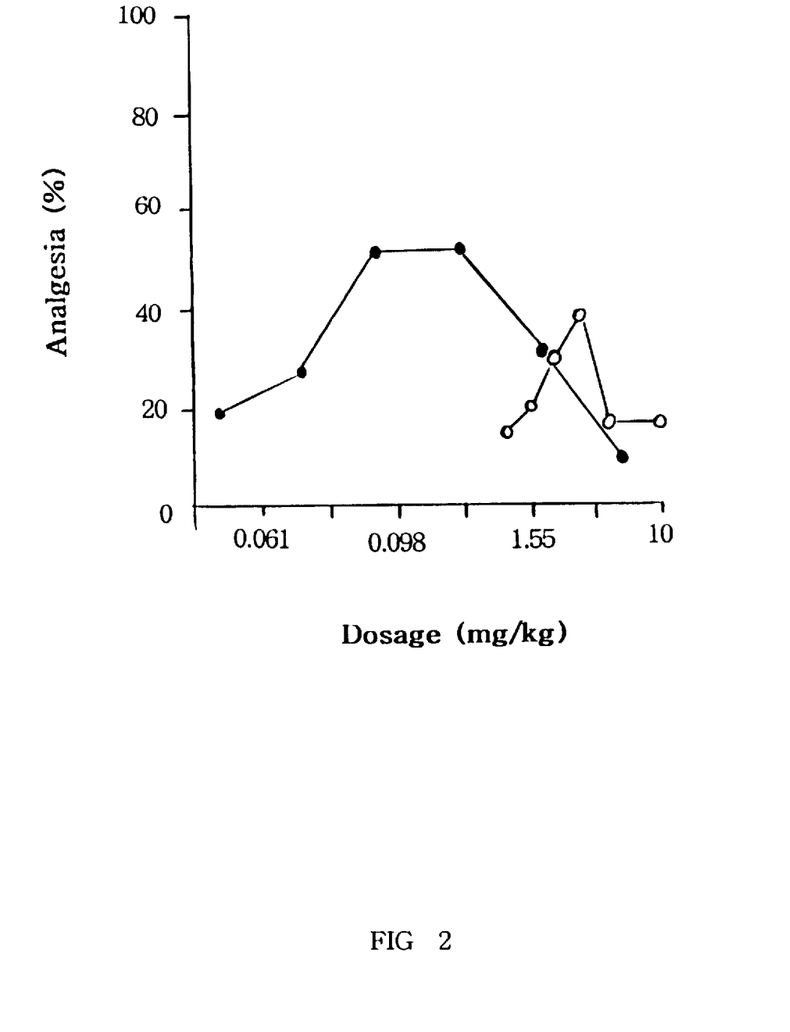
FIG. 2 shows the analgesic effects of compound of formula (I)b (●) and buprenorphine (○) in the hot plate test in mice.

The compound of formula (I)b was different from the compound of formula (I)a. It failed to produce analgesia in the hot plate test, but be effective in acetic acid writhing test with almost the same potency with buprenorphine (FIG. 2). This failure of effect against higher stimulus intensity perhaps be expected for a partial agonist (Table 2).

TABLE 2

| $ED_{50}$ value of compound of formula (I)b in the acetic acid writhing test in mice | |
| --- | --- |
| Compounds | $ED_{50}$ (95% confidence limits) |
| Compound of formula (I)b | 11.08 µg/kg (6.63~18.51) |
| Buprenorphine | 6.93 µg/kg (4.67~10.29) |

3. Anti-Morphine Experiments (1) Method

Hot plate test described above was employed in these experiments. Mice were injected with morphine (Mor) 24 mg/kg by subcutaneous injection prior to the injection of compounds studied. After 15 munutes, the compound of formula (I)b (112.5~1800 µg/kg) or buprenorphine (Bup) (470~3600 µg/kg) was given by subcutaneous injection, reaction latency of mouse was measured. The anti-Mor analgesic effect was expressed as percentage of inhibition. The $AD_{50}$ value (dosage required to inhibit Mor analgesia by 50%) was calculated.

(2) Result

Figure 3:
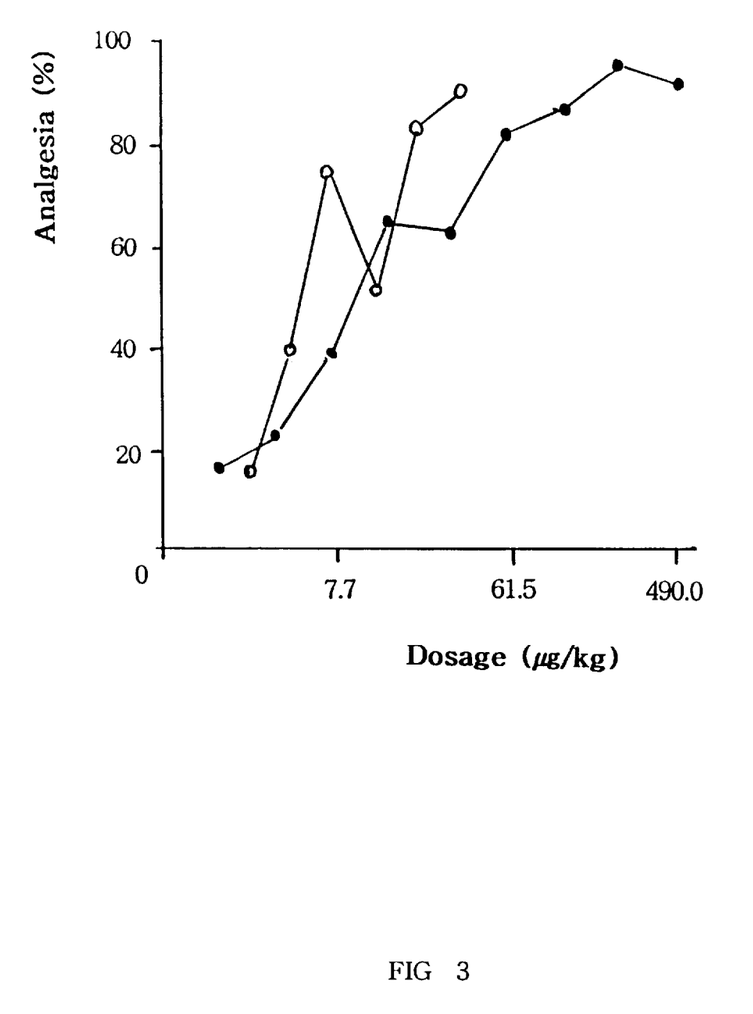
FIG. 3 shows the analgesic effects of compound of formula (I)b (●) and buprenorphine (○) in acetic acid writhing test in mice.

The compound of formula (I)b showed its anti-Mor effect using hot plate test. Results showed that the compound of formula (I)b has a significant effect against chemical nociceptive stimulus with a potency approximate to Bup, a typical partial agonist (FIG. 3, Table 2). Also like Bup, the compound of formula (I)b antagonised Mor analgesia (Table 3).

TABLE 3

Anti-morphine effect of compound of formula (I)b in the hot plate test in mice

| Compounds | $AD_{50}$ (95% confidence limits) |
|---|---|
| Compound of formula (I)a | 397.24 μg/kg (345.68~456.50) |
| Buprenorphine | 1.33 mg/kg (1.15~1.56) |

The present invention can be explained more concretely by following examples. However, the scope of this invention shall not be limited to following examples.

(Example 1) Preparation of 7 α-acetyl-6,14-endoetheno tetrahydro thebaine (III)

Thebaine (II) (2g, 6.43 mmole) with methyl vinyl ketone 910 ml) were heated and refluxed for 1 hour. Excess unsafurated ketone was removed by distillation under reduced pressure, and residue was dissolved in boiled methanol (5 ml). The mixed solution was vigorously stirred in ice bath. Formed pale brown crystalline solid was filtered, and washed with cooled methanol and dried under reduced pressure. Finally, the compound (III) was obtained in 92% yield (2.25g).

(Example 2) Preparation of 7 α-acetyl-6,14-endoethano tetrahydro thebaine (IV)

7 α-acetyl-6,14-endoetheno tetrahydro thebaine (III) (1.0 g, 2.6 mmole) was dissolved in 40 ml of ethanol, and hydrogenated with 5% palladium catalyst (0.2 g) for 30 hours in room temperature. The pressure of hydrogen maintained in 60 psi. The catalyst was filtered and removed from reaction mixture, and the mixed solution was concentrated. Finally, compound (IV) was obtained at 80% yield by recrystallization of formed product in ethanol.

(Example 3) Preparation of 6,14-endoethano-7-(2-hydroxy-2-cyclopropyl -2-ethyl)-tetrahydrothebaine (V)

In a round flask, the air was replaced by nitrogen gas and cyclopropyl magnesium bromide (13.7 mmole) was laid on. 10 ml of benzene was added for elevating the boiling point and the mixture was refluxed. During the refluxing, the solution dissolved with compound (IV) (1.05g, 2.74 mmole) in 15ml of benzene was added drop by drop to the mixture. After refluxing for about 1 hour 30 mintues, the mixture was cooled in room temperature, and saturated ammonium chloride and solvent were removed under reduced pressure. Finally, compound (V) (691mg, 60%) was obtained by purifying the residue using flash column chromatography.

(Example 4) Preparation of 6,14-endoethano-7-(2-hydorxy-2-cycloproyl- 2-ethyl)-tetrahydro oripavine (I)a Compound (V) (1.1 lg, 2.6 mmole) was laid on 15 ml of diethylene glycol dissolved with KOH (4.3 g, 77 mmole) at about 140° C. The mixture was stirred and heated at 210~230° C., and reacted for 12 hours. After finishing the reaction, the mixture was cooled at about 0C, and 10ml of ice-water and saturated ammonium chloride solution were added. The produced solid precipitate was collected and extracted using methylene chloride. Then, solid product (60%) was obtained by separating the precipitate using flash column chromatography.

¹H-NMR (CDCl₃):δ 6.68(d, 1H; J=8.0Hz), 6.52(d, 1H; J=8.0Hz), 5.00(s, 1H), 4.40(s, 1H), 3.51(s, 3H), 3.11(d, 1H; J=18.48Hz), 2.90(m, 1H), 2.70(d, 1H; J=6.24Hz), 2.46(m, 1H), 2.32(s, 4H), 2.35~2.18(m, 1H), 2.07(ddd, 1H), 1.94(t, 1H), 1.77(t, 2H), 1.66(dd, 1H), 1.31(s, 3H), 1.24(q, 1H), 1.06(m, 1H), 0.84(m, 2H), 0.48(dd, 2H), 0.28(dd, 2H)

¹³C—NMR (CDCl₃):δ145.76, 137.64, 132.26, 128.15, 119.59, 116.75, 97.39, 80.39, 73.88, 61.50, 52.80, 47.52, 46.50, 43.65, 36.22, 35.54, 31.95, 29.95, 22.77, 22.16, 20.84, 17.93, 0.86

(Example 5) Preparation of N-cyano-6,14-endoethano-7-(2-hydroxy-2- cyclopropyl-2-ethyl)-tetrahydro thebaine (VI)

Compound (V) (2 g, 4.8 mmole) was dissloved in 20 ml of chloroform, and BrCN (1.6 g, 15 mmole) was added to mixed solution. After stirring the mixture for 4 hours, the solvent was removed. The solid product was obtained by vacuum dry. Finally, pure compound (VI) was obtained at 88% yield by recrystallization of formed product in ethanol.

(Example 6) Preparation of 6,14-endoethano-7-(2-hydroxy-2-cyclopropyl -2-ethyl)-tetrahydro thebaine (VII)

Compound (VI) (1.32 g, 32 mmole) was dissolved in 1,4-dioxene, and 30% H₂)₂ (14.4 ml, 12.8 mmole) was added. 8 ml of 2N-NaOH solution was added drop by drop to the mixture with stirring. At that time, oxygen and heat was produced. After 40 minutes, no more oxygen was produced and the temperature became down. At this point, the reaction mixture was extracted and using chloroform, and urea type compound (VII) was obtained by drying under reduced pressure. This urea type compound (VII) (1.2 g, 2.72 mmole) and KOH (0.88 g, 16 mmole) was stirred and reacted using 40 ml of diethylene glycol at 170°~190° C. for 4 hours. After reaction, the mixture was cooled at about 0 °C. and 60 ml of distilled water was added. Finally, compound (VIII) (0.96 g, 88%) was obtained by filtering, washing and drying the formed solid material.

(Example 7) Preparation of N-cyclopropylmethyl-6,14-endoethano-7-(2- hydroxy-2-cyclopropyl-2-ethyl)-tetrahydro northebaine (IX)

Bromomethyl cyclopropane (536 mg, 4 mmole), potassium carbonate 91g, 7.2 mmole) and compound (VIII) (1 g, 2.5 mmole) were added to 10 ml of dimethyl formamide (DMF) slowly. After complete addition, the mixture was heated at 130°~140° C. and stirred for 3 hours. Excess potassium carbonate was filtered and removed, and DMF was removed by vacuum distillation. Finally, compound (IX) was obtained by filtering and vacuum-drying the formed solid material.

(Example 8) Preparation of N-cyclopropylmethyl-6,14-endoethano-7-(2- hydroxy-2-cyclopropyl-2-ethyl)-tetrahydro nororipavine (I)b Compound (IX) (800 mg, 1.7 mmole) and NaOH (134 mg, 5.61 mmole) were suspended in 20 ml of DMF. And, n-butylthiol (504 mg, 5.61 mmole) was added slowly and refluxed for 40 minutes. Then, the mixture was cooled to about 0 ° C. and 20ml of distilled water was added. Finally, compound (I)b was obtained by filtering and recrystalling the formed solid material in ethanol.

¹H—NMR (CDCl₃): δ 6.69(d, 1H; J=7.8Hz), 6.51(d, 1H; J=8.1Hz), 5.04(s, 1H), 4.42(s, 3H), 3.03~2.96(m, 3H), 2.62 (dd, 1H), 2.37~2.20(m, 4H), 2.07(ddd, 1H), 1.96(m, 1H), 1.78(t, 2H), 1.67(d, 1H), 1.32(s, 2H), 1.23(m, 1H), 0.80(m, 2H), 0.52~0.47(m, 3H), 0.36~0.32(m, 2H), 0.11(dd, 2H)

¹³C—NMR (CDCl₃) δ 145.76, 137.52, 132.65, 128.49, 119.67, 116.61, 97.68, 80.57, 74.04, 60.03, 58.50, 52.89, 47.70, 47.33, 43.95, 36.14, 35.76, 31.98, 30.09, 22.91, 22.73, 20.92, 18.00, 9.62, 4.38, 3.59, 0.97

(Example 9) Preparation of 6,14-endoethano-7-(2-hydroxy-2-cyclobutyl -2-ethyl)-tetrahydrothebaine (V)

In a round flask, the air was replaced by nitrogen gas and cyclobutyl magnesium bromide (9.59 mmole) was laid on. 7ml of benzene was added for elevating the boiling point and the mixture was refluxed. During the refluxing, the solution dissolved with compound (IV) (735mg, 1.92 mmole) in 11 ml of benzene was added drop by drop to the mixture. After refluxing for about 1 hour 30 mintues, the mixture was cooled in room temperature, and saturated ammonium chloride and solvent were removed under reduced pressure. Finally, compound (V) (523 mg, 62%) was obtained by purifying the residue using flash column chromatography.

(Example 10) Preparation of 6,14-endoethano-7-(2-hydorxy-2-cyclobutyl -2-ethyl)-tetrahydro oripavine (I)c

Compound (V) (686 mg, 1.56 mmole) was laid on 9 ml of diethylene glycol dissolved with KOH (2.58 g, 46.2 mmole) at about 140° C. The mixture was stirred and heated at 210°~230° C., and reacted for 12 hours. After finishing the reaction, the mixture was cooled at about 0° C., and 6 ml of ice-water and saturated ammonium chloride solution were added. The produced solid precipitate was collected and extracted using methylene chloride. Then, solid product (60%) was obtained by separating the precipitate using flash column chromatography.

$^1$H-NMR (CDC$_3$) : δ 6.70(d, 1H; J=8.07Hz), 6.53(d, 1H; J=8.04Hz), 5.21(s, 1H), 4.39(s, 1H), 3.52(s, 3H), 3.11(d, 1H; J=18.51lHz), 2.70~2.60(m, 2H), 2.48~2.24(m, 2H), 2.31(s, 1H), 2.20~2.08(m, 1H), 1.96(ddd, 1H), 1.84~1.62(m, 8H), 1.17(s, 3H), 1.13~1.00(m, 2H), 0.80(m, 1H)

$^{13}$C—NMR (CDCl$_3$) δ 145.59, 131.97, 127.84, 119.45, 116.69, 96.90, 80.14, 75.30, 61.23, 52.60, 43.25, 42.95, 35.90, 35.31, 31.39, 29.69, 21.95, 21.52, 21.18, 20.03, 17.86, 16.57

We claim:

1. Buprenorphine analgesic analogues represented by the following formula(I) and their non-toxic pharmaceutically acceptable salt.

wherein R$_1$ is hydrogen atom, methyl, ethyl or cyclopropyl or cyclobutyl:

and

R$_2$ is cyclopropyl.

2. Buprenorphine analgesic analogues according to claim 1, wherein the compound is represented by following formula (I)a:

3. Buprenorphine analgesic analogues according to claim 1, wherein the compound is represented by the following formula (I)b

* * * * *

UNITED STATES PATENT AND TRADEMARK OFFICE
CERTIFICATE OF CORRECTION

PATENT NO.   :   5,849,915

DATED   :   15 December 1998

INVENTOR(S)   :   Yong Hae KIM et al.

It is certified that error appears in the above-identified patent and that said Letters Patent is hereby corrected as shown below:

| Column | Line | |
|---|---|---|
| 6 | 40 | Change "be" to --was--. |
| 6 | 63 | After "injection" insert --,--. |
| 9 | 36 | Change "salt" to --salts:--. |

Signed and Sealed this

Eighth Day of February, 2000

Attest:

Q. TODD DICKINSON

*Attesting Officer*          *Commissioner of Patents and Trademarks*

UNITED STATES PATENT AND TRADEMARK OFFICE
CERTIFICATE OF CORRECTION

PATENT NO. : 5,849,915
DATED : December 15, 1998
INVENTOR(S) : Yong Hae KIM et al It is certified that error appears in the above-identified patent and that said Letters Patent is hereby corrected as shown below:

Column 6, Line 63, After "injection," insert -- the --.

Signed and Sealed this

Twenty-eighth Day of March, 2000

Attest:

Q. TODD DICKINSON

Attesting Officer

Commissioner of Patents and Trademarks